US010258034B2

(12) United States Patent
Reichert et al.

(10) Patent No.: US 10,258,034 B2
(45) Date of Patent: Apr. 16, 2019

(54) COATED SEED AND METHODS FOR REDUCING SEED DUST

(71) Applicant: BAYER CROPSCIENCE LP, Research Triangle Park, NC (US)

(72) Inventors: Ronald Reichert, Cary, NC (US); William G. Hairston, Wake Forest, NC (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

(21) Appl. No.: 14/391,972

(22) PCT Filed: Mar. 15, 2013

(86) PCT No.: PCT/US2013/031888
§ 371 (c)(1),
(2) Date: Oct. 10, 2014

(87) PCT Pub. No.: WO2013/158284
PCT Pub. Date: Oct. 24, 2013

(65) Prior Publication Data
US 2015/0072857 A1  Mar. 12, 2015

Related U.S. Application Data

(60) Provisional application No. 61/619,691, filed on Apr. 3, 2012.

(51) Int. Cl.
*A01N 25/24* (2006.01)
*A01N 25/10* (2006.01)
*A01N 25/00* (2006.01)
*A01C 1/06* (2006.01)
*A01N 43/78* (2006.01)

(52) U.S. Cl.
CPC ............... *A01N 25/10* (2013.01); *A01C 1/06* (2013.01); *A01N 25/00* (2013.01); *A01N 25/24* (2013.01); *A01N 43/78* (2013.01)

(58) Field of Classification Search
CPC ........ A01N 25/00; A01N 43/78; A01N 25/12; A01N 25/24; A01N 25/08
See application file for complete search history.

(56) References Cited

U.S. PATENT DOCUMENTS

| | | | |
|---|---|---|---|
| 2,777,776 A | 1/1957 | Kieras | |
| 3,480,456 A | 11/1969 | Forkner | |
| 3,808,740 A | 5/1974 | Porter et al. | |
| 3,905,152 A | 9/1975 | Loperfido | |
| 4,002,706 A | 1/1977 | Pretorius | |
| 4,285,994 A | 8/1981 | Pearce et al. | |
| 4,291,245 A | 9/1981 | Nowlin et al. | |
| 5,876,739 A * | 3/1999 | Turnblad ............ | A01C 1/06 424/406 |
| 5,968,222 A | 10/1999 | Kodali | |
| 8,053,223 B2 | 11/2011 | Meikle et al. | |
| 9,380,739 B2 | 7/2016 | Jessop | |
| 2001/0056177 A1* | 12/2001 | Becker .................. | C12N 9/98 530/300 |
| 2004/0020114 A1 | 2/2004 | Boehmer et al. | |
| 2007/0105717 A1 | 5/2007 | Heinrichs et al. | |
| 2007/0207927 A1 | 9/2007 | Rosa et al. | |
| 2012/0065060 A1* | 3/2012 | Reus ..................... | A01C 1/06 504/100 |
| 2012/0115911 A1* | 5/2012 | Ochampaugh ........ | A01C 1/00 514/341 |
| 2015/0072857 A1 | 3/2015 | Reichert et al. | |
| 2015/0267063 A1 | 9/2015 | Drewer et al. | |

FOREIGN PATENT DOCUMENTS

| | | |
|---|---|---|
| CA | 2750194 A1 | 7/2011 |
| CN | 1180061 A | 4/1998 |
| CN | 1357217 A | 10/2002 |
| EP | 0010630 A1 | 5/1980 |
| EP | 10735846 A4 | 12/2011 |
| JP | 3949842 B2 | 9/2000 |
| JP | 3949842 B2 | 7/2007 |
| WO | 9011011 A1 | 10/1990 |
| WO | 0035277 A1 | 6/2000 |
| WO | 2004049778 A1 | 6/2004 |
| WO | 2005077169 A1 | 8/2005 |
| WO | 2006060272 A2 | 6/2006 |
| WO | 2007103076 A1 | 9/2007 |
| WO | 2010087380 A1 | 8/2010 |
| WO | 2010107312 A1 | 9/2010 |
| WO | 2011148144 A1 | 12/2011 |
| WO | 2012025621 A1 | 3/2012 |
| WO | 2012143674 A2 | 10/2012 |
| WO | 2013/023007 A1 | 2/2013 |
| WO | 2013150261 A1 | 10/2013 |

OTHER PUBLICATIONS

International Search Report from corresponding PCT/US2013/031888, dated Jun. 17, 2013.
Endlein and Peleikis, "Natural Waxes-Properties, Compositions and Applications," 2011, pp. 1-8, vol. 137, SOFW Journal.
Kuznesof, "Beeswax," Chemical and Technical Assessment, 65th JECFA, Jun. 2005.
Aginnovation Seed Flow Meter (Information Sheet).
Syngenta presentation (Ray Elliott), Feb. 9, 2011.
Hartmann et al., "Techniques of Seed Production and Handling" (Chapter Six), 2010, Eighth Edition, Hartmann & Kester's Plant Propagation: Principles and Practices.
Baird et al., "Evaluation of Seed Treatments on Shrunken-2 Sweet Corn," 1994, pp. 817-821, vol. 78, Plant Disease.
Shao et al., "The Outermost Cuticle of Soybean Seeds: Chemical Composition and Function during Imbibition," 2007, pp. 1071-1082, vol. 58, Issue 5, J. Exp. Botany.
De Souza and Marcos-Filho, "The Seed Coat as a Modulator of Seed-Environment Relationships in Fabaceae," 2001, pp. 365-375, vol. 24, Issue 4, Revta Brasil. Bot., Sao Paolo.

(Continued)

*Primary Examiner* — Johann R Richter
*Assistant Examiner* — Danielle Sullivan

(57) ABSTRACT

Methods for reducing dust by treating a seed with a lubricant composition are described herein. The disclosure also provides for a method of reducing planter dust released during seed planting by applying a lubricant composition to a seed. Methods for increasing seed lubricity by coating a seed with a lubricant composition are also described. Compositions and seeds useful in these methods are also described.

6 Claims, 8 Drawing Sheets

(56) References Cited

OTHER PUBLICATIONS

Yan et al., "Analysis of the Chemical Composition of Cotton Seed Coat by Fourier-transfer Infrared (FT-IR) Microspectroscopy," 2009, pp. 1099-1107, vol. 16, Cellulose.
Duenas et al., "Proanthocyanidin Composition in the Seed Coat of Lentils," 2003, pp. 7999-8004, vol. 51, Issue 27, J. Agric. Food Chem.
Ross et al., "Understanding Water Uptake from the Induced Changes Occurred during Processing: Chemistry of Pinto and Navy Bean Seed Coats," 2010, pp. 631-647, vol. 13, Int. J. of Food Properties.
Leopold Center for Sustainable Agriculture Competitive Grant Report 89-01, "Seed Coating with Environmentally Acceptable Polymers as an Alternative to Fungicide Treatment of Corn and Soybeans," 1993, pp. 81-94.
NC Extension, "Precision Seeding for Vegetable Crops," Aug. 31, 1994.
Brown et al., "Corn Insecticide Seed Treatment Options," Jan. 22, 2013.
Precision Laboratories, Prism label, Jan. 2015.
Zeng and Shi, "Preparation and Application of a Novel Environmentally Friendly Organic Seed Coating for Rice," 2008, pp. 19-25, vol. 1, Issue 2, American-Eurasian J. of Agronomy.
Šimic et al., "Stored Grain Losses," 2006, pp. 59-63, Proc. of the 9th Intern. Working Conf. on Stored Product Protection, Brazil.
Basavaraj et al., "Effect of Fungicide and Polymer Film Coating on Storability of Onion Seeds," 2008, pp. 212-218, vol. 21, Issue 2, Karnataka J. Agric. Sci.
Manjunatha et al., "Effect of Seed Coating with Polymer, Fungicide and Containers on Seed Quality of Chilli during Storgae," 2008, pp. 270-273, vol. 21, Issue 2, Karnataka J. Agricul. Sci.
De Almeida et al, "Polymer Coating, Germination and Vigor of Broccoli Seeds," 2005, pp. 221-226, vol. 62, Issue 3, Sci. Agric. (Piracicaba Braz.).
Giang and Gowda, "Influence of Seed Coating with Synthetic Polymers and Chemicals on Seed Quality and Storability of Hybrid Rice," 2007, pp. 68-74, vol. 15, Omonrice.
Shakuntala et al., "Polymer Film Coating for Precision Seeding in Sunflower," 2012, pp. 339-340, Proc. of Agro-Informatics and Precision Agriculture.
Duan and Burris, "Film Coating Impairs Leaching of Germination Inhibitors in Sugar Beet Seed," 1997, pp. 515-520, vol. 37, Crop Sci.
Thobunluepop et al, "The Perspective Effects of Various Seed Coating Substances on Rice Seed Variety Khao Dawk Mali 105 Storability I: The Case Study of Physiological Properties," 2008, pp. 2291-2299, vol. 11, Issue 19, Pakistan J. of Biol. Sci.
Bao, Zhi-Juan, "Effect of Electret Membrane on Activity of Seeds," 2006, pp. 501-505, vol. 44, Issue 3, Journal of Jilin University (English abstract).
Eguchi, "On the Permanent Electret", Philosophical Magazine, (1925), vol. 49, pp. 178-192.
File History of U.S. Appl. No. 14/375,361.
Wikipedia webpage "Electret" (revision Dec. 15, 2015).
Exosect Press Release, "Exosect CEO, Martin Brown, to address CropWorld North America conference 2012," Feb. 6, 2012.
Exosect Press Release, "Exosex SPTab launched at Expocida," Feb. 23, 2012.
Heaviside, "Electrical Papers," 1892, pp. 488-493, Chelsea, New York.
G. M. Sessler, ed., "Topics in Applied Science, Electrets" 2d ed. 1987, vol. 33.
V. N. Kestelman et al., eds., "Electrets in Engineering: Fundamental and Applications," 2000.
Jefimenko & Walker, "Electrets," The Physics Teacher, 1980, pp. 651-659.
Garbassi, Morra & Occiello, "Polymer Surfaces: From Physics to Technology," 1998, John Wiley & Sohn Ltd., Chichester.
Sheikholeslami & Gulak, "Proceedings of the IEEE," 2000, vol. 88, Issue 5.
Colin Campbell, "Surface Acoustic Wave Devices and their Signal Processing Applications," 1989.
Bao, Journal of Jilin Agricultural University, 2006, pp. 481-485, vol. 28, No. 5.
Alphonsus V. Pocius, "Adhesion and Adhesives Technology," 2012, 3d ed.
Thomas Kallard, ed., "Electret Devices for Air Pollution Control," 1972.
Wolfgang Ensinger, Print of definition of "Electrete," Aug. 2006, RÖMPP, Georg Thieme Verlag KG.
David Firestone, ed., "Physical and Chemical Characteristics of Oils, Fats, and Waxes," 2013, 3d edition.
David R. Lide, ed., "CRC Handbook of Chemistry and Physics," 2007-2008, 88th Edition.
Declaration of Dr. Curt Reschke, executed Mar. 31, 2017, Submitted in PGR2017-00018.
Declaration of Peter N. Marks, executed Mar. 31, 2017, submitted in PGR2017-00018.
Gonzalez-Tello, "Analysis of the Mean Diameters and Particle-Size Distribution in Powders," 2010, pp. 158-164, 27, Part. Syst. Charact.
Lubrizol Technical Data Sheet, "Lanco™ TF 1780 and Lanco™ TF 1780EF," May 2011.
Lubrizol Technical Data Sheet, "Lance™ 1890," Jun. 2007.
Corson, Dale and Lorrain, Paul, "Introduction to Electromagnetic Fields and Waves," 1962, p. 30 and pp. 143-145, W. H. Freeman and Company.
Schein, L.B., "Electro-photography and Development Physics," 1992, p. 79, 2nd Edition, Springer-Verlag (ISBN 3-540-55858-6, ISBN 0-387-55858-6).
Chemistry: LibreTexts™, "Van Der Waals Interactions," NSF and University of California-Davis (last updated Oct. 22, 2015).
J. H. Rayner and G. Brown, "Properties of Talc (Hydrated magnesium silicate) taken from 'The Crystal Structure of Talc'," Clays and Clay Minerals, 1973, pp. 103-114, vol. 21, Chapter 2, Pergamon Press, Hefts, England (Received Aug. 28, 1972).
Appendix A, Calculation by Dr. Reschke, prepared Mar. 2017.
Michelman, "Michem® Wax," 2008 (accessed at http://doc.doculead.com/doc/Michelman-Inc/Michelman-Michem-Wax-500-Wax-Powders/2009041102/#0).
Rich Keller, "CropWorld" (article whose focus was on sharing crop technology), Mar. 30, 2012, AgWorld.
Clare Storm, "A new mycoinsecticide for treatment of grain storage," 5th Annual Biocontrol Industry Meeting (ABIM Lucerne, Switzerland Oct. 25-26, 2010).
Exosect Press Release, Mar. 29, 2012.
ICIS Chemical Business, "Waxes Find Niche Application in Crop Protection," Apr. 1, 2002.
The Royal Society of Chemistry, "Pesticide Outlook—Oct. 2001" (R&D News), 2001.
Peter Marks CV, Mar. 2017.
Kaufman, "Technology and Product Reports," 1991, pp. 99-102, HortTechnology.
Burris, "Proc. of the 47th Annual Corn and Sorghum Ind. Res. Conf.," 1992, pp. 33-43.
Ohio State University Extension Bulletin 638, 2001.
Dr. Curt Raschke CV, Mar. 2017.
Priestly and Leopold, "Alleviation of Imbibitional Chilling Injury by Use of Lanolin," 1986, pp. 1252-1254, vol. 26, Crop Sci.
Michelman, "Wax Emulsions—Formulation and Properties of Wax Emulsions for Coatings and Industrial Applications," 2009, pp. 1-9.
Copeland et al., "Seed Treatment for Field Crops," Jul. 1994, pp. 1-8, Mich. State Univ. Extension publication E-1199.
Avipel label, Feb. 24, 2012.
Pixy label, Jul. 17, 2015.
Helmenstine, Anne Marie, "What is Camauba Wax," https://www.thoughtco.com/what-is-camauba-wax-607371 (last updated Mar. 26, 2016).
Press release Log (PRLog) citation of "Exosect CEO, Martin Brown, to address CropWorld North America conference 2012" (dated Feb. 6, 2012).
WayBackMachine, http://archive.org/web/; citation of https://www.prlog.org/11791416-exosect-ceo-martin-brown-to-address-cropworld-north-america-conference-2012.html.
Entostat web printout (printed Mar. 15, 2017).
Wax facts: 1-9 (https://www.afpm.org/waxfacts), 2017.

* cited by examiner

COATED SEED AND METHODS FOR REDUCING SEED DUST

CROSS REFERENCE TO RELATED APPLICATIONS

This application is a § 371 National Stage Application of PCT/US2013/031888, filed Mar. 15, 2013, which claims priority to U.S. Provisional Application No. 61/619,691, filed on Apr. 19, 2012.

BACKGROUND

Field of the Invention

Methods for reducing dust emission by treating or coating a seed with a lubricant composition are described. The disclosure also provides for methods of planter dust released during seed planting by applying a lubricant composition to a seed. Methods for increasing seed lubricity by coating a seed with a lubricant composition are also described. Compositions and seeds useful in these methods are also described.

Description of Related Art

It is believed that vacuum planters release a certain amount of dust during the planting of seeds. It is also believed that the amount of seed dust released during seed planting depends on a variety of factors, such as the technique or mechanism employed during seed planting. Other factors contributing to seed dust associated with planting include the type of seed coating used during planting. It is believed that while traditional planter lubricants, such as talc and graphite, provide lubrication to help seed flow through the planter mechanism, such traditional planter lubricants may not possess a high enough level of lubricity to prevent some level of seed attrition that may result in the loss of small amounts of insecticide from the seed surface. As such, there is a need to find an alternative to traditional planter lubricants that are capable of limiting insecticidal dust emissions during seed planting. To this end, the disclosed compositions and methods have the ability to reduce or control seed and planter dust in a manner that was not previously recognized.

SUMMARY

In an aspect, the disclosure provides for a method of reducing dust emission by applying a lubricant composition to a seed. In another aspect, the dust emission is reduced relative to a seed coating comprising talc or graphite. In yet another aspect, the pollinating insect is a bee and the dust emission is released from a mechanical seed planter.

In another aspect, the disclosure provides for a method of treating a seed by coating a seed with a lubricant composition, wherein the lubricant composition reduces the emission of insecticidal, pesticidal, fungicidal, or herbicidal dust. In another aspect, the lubricant composition reduces the emission of clothianidin dust.

In an aspect, the disclosure provides for a coated seed comprising an active insecticidal, fungicidal, pesticidal, or herbicidal treating agent and a lubricant composition. In another aspect, the lubricant composition is an organic lubricant composition coating. In an aspect, the lubricant composition is a wax composition. In yet another aspect, the lubricant composition is selected from the group consisting of polyethylene wax, carnuba wax, paraffin wax, polypropylene wax, and oxidized polyethylene wax. In another aspect, the seed is a corn seed. In yet another aspect, the lubricant composition is applied to a seed at about 1.0-3.0 oz/cwt or about 0.5-4.0 oz/cwt.

DETAILED DESCRIPTION OF A PREFERRED EMBODIMENT

Figure 1:
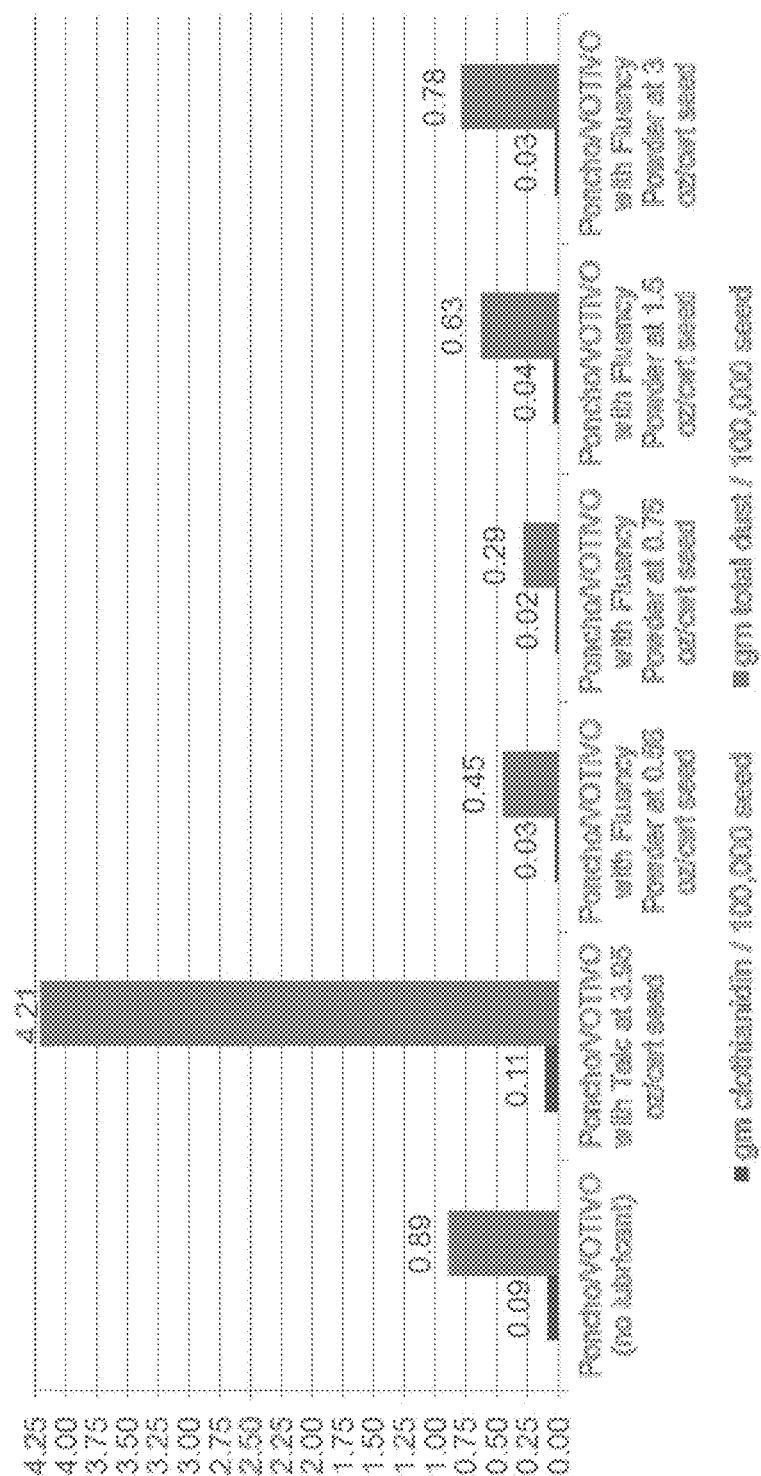
FIG. 1 sets forth the total grams of dust per 100,000 kernels and grams of clothianidin in total dust per 100,000 kernels for seeds treated with a Poncho/VOTiVO and talc treatment as compared to a treatment of Poncho/VOTiVO and polyethylene wax used as a lubricant at 0.56 oz/cwt seed, 0.75 oz/cwt seed, 1.5 oz/cwt seed, and 3 oz/cwt seed as measured by a John Deere Vacuum Meter.

The disclosure provides for a method of reducing dust emission, pesticidal dust, insecticidal dust, herbicidal and/or fungicidal dust. In another aspect, the disclosure provides for a method of reducing dust emission, pesticidal dust, insecticidal dust, herbicidal and/or fungicidal dust by coating a seed with a composition described herein, for example a lubricant composition. In yet another aspect, the disclosure provides for a method of reducing dust emission, pesticidal dust, insecticidal dust, or fungicidal dust by:

(1) applying a treating agent to a seed; and
(2) applying a lubricant composition to the treated seed such that the lubricant composition reduces dust emission, pesticidal dust, insecticidal dust, herbicidal and/or fungicidal dust.

In an aspect, the disclosure provides for a method of coating a seed with a treating agent and a lubricant composition described herein, for example a wax composition, wherein the coated seed emits a reduced amount of dust, pesticidal dust, insecticidal dust, or dust.

The disclosure also provides for a method of reducing vacuum planter dust released during planting. In an aspect, the disclosure provides for a method of reducing insect exposure to vacuum planter dust released during planting. In another aspect, the vacuum planter dust is an insecticidal, pesticidal, or fungicidal dust.

In an aspect, the disclosure provides for a method of improving seed flow by applying or treating seed with a composition described herein. In another aspect, a composition described herein is applied to wet seed. The disclosure also provides for a method of increasing seed lubricity by coating a seed with a composition described herein. In an aspect, the disclosure provides for a method of lowering lubricity at lower use rates than those afforded by the coating of a seed with talc or graphite. The disclosure also provides for a method increasing the level of lubricity in an amount that is sufficient to reduce seed attrition that may result in the loss of small amounts of insecticide from the seed surface.

The disclosure also provides for a method of adding a treating agent and a wax to a seed. In another aspect, a wax composition is added to a pre-treated seed prior to the pre-treated seed being placed in soil. In another aspect, a seed is pre-treated by both a treating agent and a wax composition described herein prior to planting. In yet another aspect, a composition described herein can be applied to seed in a planter or hopper either manually or with a mechanized system, such as a mechanized metering system. In an aspect, the powder form of a wax is added to seed in a planter.

In an aspect, a treating agent is added to a seed prior to placing seed into a bag or container for shipping to a planting site. In another aspect, after the seed arrives at the planting site, a lubricant composition described herein is added to the seed. In yet another aspect, a lubricant composition described herein is added to pre-treated seed (seed previously treated with a treating agent) in a planter mechanism or hopper of the planting mechanism. In another aspect, a treating agent and a lubricant composition are added to a seed prior to the seed being loaded on a planter or hopper for planting. In yet another aspect, a treating agent and a first lubricant composition are added to seed prior to the seed being loaded on a planter or hopper for planting and a second lubricant composition are added to seed in the planter or hopper.

In an aspect, the dust, insecticidal dust, herbicidal dust, pesticidal dust, or fungicidal dust emission is reduced relative to traditional lubricants, such as talc or graphite. In yet another aspect, a lubricant composition described herein, for example a wax composition, reduces the dust, insecticidal dust, herbicidal dust, pesticidal dust, or fungicidal dust emission from the planter mechanism, such as an air or vacuum planter. In an aspect, the planter mechanism is a John Deere, Case IH, Kinze, AGCO White, Great Plains, or Precision Planting vacuum planter.

The disclosure also provides for a method of reducing active agent dust, pesticide, herbicidal, fungicide, or insecticide dust exposure to an insect by applying a composition described herein to a seed. In an aspect, the insect can be a pollinating insect. In another aspect, the insect can be an insect capable of being negatively influenced by the presence of a pesticide, fungicide, herbicidal, or insecticide dust. In yet another aspect, the insect is a bee. In another aspect, the bee is a Western honey bee, European honey bee (*Apis mellifera*), or Africanized honey bee.

In an aspect, a composition capable of being used with the methods described herein comprises, consists essentially of, or consists of a lubricant composition. In another aspect, a composition capable of being used with the methods described herein comprises, consists essentially of, or consists of a wax, polyethylene wax, powdered polyethylene wax, or Michem®Wax 437 (Michelman).

In an aspect, a composition described herein can include one or more lubricant compositions. In another aspect, a lubricant composition is an organic lubricants. In another aspect, the lubricant composition is a wax, for example, polyethylene, powdered polyethylene, carnuba, paraffin, polypropylene, an oxidized polyethylene wax, montan waxes, microcrystalline waxes, Fischer-Tropsch waxes, amide waxes, Ethylene-Acrylic-Acid (EAA) waxes, polyolefin waxes, Ethylene bis stearamide (EBS) waxes, animal waxes (bees wax & lanolin), vegetable waxes (carnauba & candelilla), or slac and scale waxes. In another aspect, a lubricant composition is Teflon (polytetrafluoroethylene).

In an aspect, a composition capable of being used with the methods described herein comprises, consists essentially of, or consists of a treatment agent and a lubricant composition, for example, a wax. In another aspect, a composition capable of being used with the methods described herein comprises, consists essentially of, or consists of a treatment agent together with a polyethylene wax or powdered polyethylene wax. In an aspect, the wax is used as a planter lubricant.

In an aspect, a treatment agent is a compound or composition exhibiting insecticidal, pesticidal, or fungicidal properties. In another aspect, a treatment agent is a compound or composition with neonicotinoid properties. In an aspect, a treating agent is selected from the group consisting of acetamiprid, clothianidin, dinotefuran, imidacloprid, nitenpyram, thiacloprid, thiamethoxam, abamectin, Nipsit INSIDE® (Valent), Platinum® (Syngenta), Admire® Pro (Bayer CropScience), Cruiser (Syngenta), Gaucho (Bayer CropScience), Leverage® (Bayer CropScience), Actara (Syngenta), Venom (Valent), Provado® (Bayer CropScience), Alias (Mana), Pasada (Mana), Couraze (Cheminova), Assail® (DuPont), Poncho®/VOTiVO™ (Bayer CropScience), Poncho® Beta (Bayer CropScience), and/or Poncho® 1250+VOTiVO™ (Pioneer). In an aspect, the treatment agent is applied to a seed and the seed is subsequently coated with a lubricant compound.

In an aspect, insecticidal dust, pesticidal dust, or fungicidal dust is dust from one or more of the following actives: acetamiprid, clothianidin, dinotefuran, imidacloprid, nitenpyram, thiacloprid, thiamethoxam, abamectin, Nipsit INSIDE® (Valent), Platinum® (Syngenta), Admire® Pro (Bayer CropScience), Cruiser (Syngenta), Gaucho (Bayer CropScience), Leverage® (Bayer CropScience), Actara (Syngenta), Venom (Valent), Provado® (Bayer CropScience), Alias (Mana), Pasada (Mana), Couraze (Cheminova), Assail® (DuPont), Poncho®/VOTiVO™ (Bayer CropScience), Poncho® Beta (Bayer CropScience), and/or Poncho® 1250+VOTiVO™ (Pioneer). In an aspect, the treatment agent is applied to a seed and the seed is subsequently coated with a lubricant compound. In another aspect, "dust" can include any active agent coated on a seed that is emits a particulate or "dust." In another aspect, dust is released during the planting process.

In an aspect, a composition described herein includes a mixture or combination of lubricant composition and treatment agent described herein.

In another aspect, a composition or method described herein does not include an inorganic lubricant composition. Inorganic compounds, for example talc and graphite, encompass compounds such as carbides, carbonates, simple oxides of carbon, cyanides, and allotropes of carbon.

In an aspect, a composition or method described herein does not include talc. In another aspect, a composition or method described herein does not include graphite or graphite blends. In yet another aspect, a composition or method described herein does not include blends of graphite and/or talc. In another aspect, a composition or method described herein contains trace amount of talc or graphite. In another aspect, a composition or method described herein contains less than about 5%, less than about 10%, less than about 20%, less than about 20%, less than about 30%, less than about 40%, or less than about 50% by weight of talc, graphite, or a combination of talc or graphite.

In yet another aspect, a composition described herein may be blended with inert materials to improve handling or packaging, for example, silica, starches (natural and derived), clays, and other minerals.

In an aspect, a composition described herein is applied as a powder to a seed at the same time or before the planter fills the planter hopper with seed. In another aspect, a composition described herein is applied as a dry powder to a seed as a farmer fills the planter hopper with seed.

In an aspect, a composition described herein, such as a wax, is capable of providing lubricity at a lower use rate as compared to conventional lubricants, such as talc or graphite. In another aspect, a wax described herein provides for improved seed to seed and seed to planter mechanism slip and reduces insecticide loss from seed due to attrition as it passes through the vacuum planter mechanisms.

In another aspect, a lubricant composition described herein provides an increased level of lubricity to reduce seed to seed and seed to planter mechanism attrition as compared to traditional lubricant compositions, such as talc or graphite. In an aspect, a lubricant composition described herein is also effective at lower application rates than talc or graphite.

In an aspect, the methods and compositions described herein reduce dust, insecticidal dust emissions, pesticidal dust emissions, herbicidal dust emissions, or fungicidal dust emissions by about 5% to about 20%, about 20% to about 60%, about 40% to about 70%, about 50% to about 90%, about 60% to about 80%, about 65% to about 95%, about 80% to about 95%, or about 5%, about 15%, about 25%, about 40%, about 50%, about 60%, about 70%, about 80%, about 90%, or about 95%, or about 5% or more, about 15% or more, about 25% or more, about 40% or more, about 50% or more, about 60% or more, about 70% or more, about 80% or more, about 90% or more, or about 95% or more. In yet another aspect, the dust emissions, insecticidal dust emissions, pesticidal dust emissions, or fungicidal dust emissions is reduced relative to traditional lubricants, such as talc or graphite.

In an aspect, a composition described herein is applied to a seed at a rate of about 0.1-5.0 oz/cwt (ounces/hundredweight), about 0.5-4.0 oz/cwt, about 1.0-3.5 oz/cwt, about 1.5-3.0 oz/cwt, about 2.0-3.0 oz/cwt, about 2.0-2.5 oz/cwt, or about 0.2 oz/cwt, about 0.5 oz/cwt, about 0.75 oz/cwt, about 1.0 oz/cwt, about 1.5 oz/cwt, about 2.0 oz/cwt, about 2.5 oz/cwt, about 3.0 oz/cwt, about 3.5 oz/cwt, about 4.0 oz/cwt, about 4.5 oz/cwt, about 5.0 oz/cwt, or about 0.2 oz/cwt or more, about 0.5 oz/cwt or more, about 0.75 oz/cwt or more, about 1.0 oz/cwt or more, about 1.5 oz/cwt or more, about 2.0 oz/cwt or more, about 2.5 oz/cwt or more, about 3.0 oz/cwt or more, about 3.5 oz/cwt or more, about 4.0 oz/cwt or more, about 4.5 oz/cwt or more, or about 5.0 oz/cwt or more. In yet another aspect, a composition described herein is applied to a seed in a manner sufficient to convey the desired property.

In an aspect, a composition described herein is applied to a seed in a single application step. In another aspect, a composition described herein is applied in multiple application steps. In yet another aspect, a composition described herein is applied in one, two, three or more application steps to a seed. In another aspect, a method described herein excludes multiple application steps. In an aspect, the methods described herein include a first sequential application of a treating agent described herein to a seed followed by a second application of lubricant composition described herein to a seed.

Seeds which can be treated by the methods described herein include, for example, seeds that are treated with insecticides, pesticides, or fungicides. Seeds may include any agricultural or vegetable seeds that are planted through a vacuum planter, including wherein talc may be used as a planter lubricant. In an aspect, the seed is selected from the group consisting of a corn seed, cotton seed, sorghum seed, oat seed, rye seed, barley seed, soybean seed, vegetable seed, wheat seed, sugarbeet seed, rice, sunflower seed, lettuce seed, and spinach seed. In an aspect, the seed is corn seed. Examples of corn seeds capable of being used in the methods described herein include, for instance, sweet corn (for example, *zea mays* convar. *saccharata* var. *Rugosa*), silver queen corn, golden bantam, early sunglow, indian corn, sugar corn, pole corn, field corn, dent corn, flint corn, flour corn, blue corn (for example, *Zea mays amylacea*), pop corn, and waxy corn.

Seeds may be treated with the described compositions by applying the compositions directly to the seed. In another embodiment, the seed may be treated indirectly, for example by treating the environment or habitat in which the seed is exposed to. Conventional treatment methods may be used to treat the environment or habitat including dipping, spraying, fumigating, chemigating, fogging, scattering, brushing on, shanking or injecting.

In another aspect, the disclosure provides for a kit comprising, consisting essentially of, or consisting of any of the compositions disclosed herein. In an aspect, the kit includes any of the combination of compositions described in Examples 1-4, Tables 1-8, or FIGS. 1-8. In another aspect, the kit provides for the compositions described in Examples 1-4, Tables 1-8, or FIGS. 1-8, applied in a manner that is consistent with the methodology of these examples and figures. In another aspect, the kit provides instructions or guidance regarding the use of the compositions or methods described herein.

In an aspect, the kit includes instructions describing the methodology described herein. In another aspect, the kit includes instructions describing the methodology set forth in any of Examples 1-4, Tables 1-8, or FIGS. 1-8. In an aspect, the instructions are included with the kit, separate from the kit, in the kit, or are included on the kit packaging. In yet another aspect, the instructions provide for application of a lubricant composition at planting.

The following examples serve to illustrate certain aspects of the disclosure and are not intended to limit the disclosure.

EXAMPLES

Example 1

Example 1 sets forth Poncho/VOTiVO Corn dust levels with polyethylene wax as a planter lubricant.

In Table 1, the total grams of dust per 100,000 kernels and grams of clothianidin in total dust per 100,000 kernels for seeds treated with Poncho/VOTiVO and fluency powder (polyethylene wax) as a planter lubricant were evaluated. As set forth in Table 1, a treatment combination of Poncho/VOTiVO and talc treatment was compared to a treatment combination of Poncho/VOTiVO and fluency powder (polyethylene wax) at 0.56 oz/cwt seed, 0.75 oz/cwt seed, 1.5 oz/cwt seed, and 3 oz/cwt seed. The dust and clothianidin exposure were measured with a Heubach Dustmeter. The data in Table 1 represents an average of two seed sources.

Figure 2:
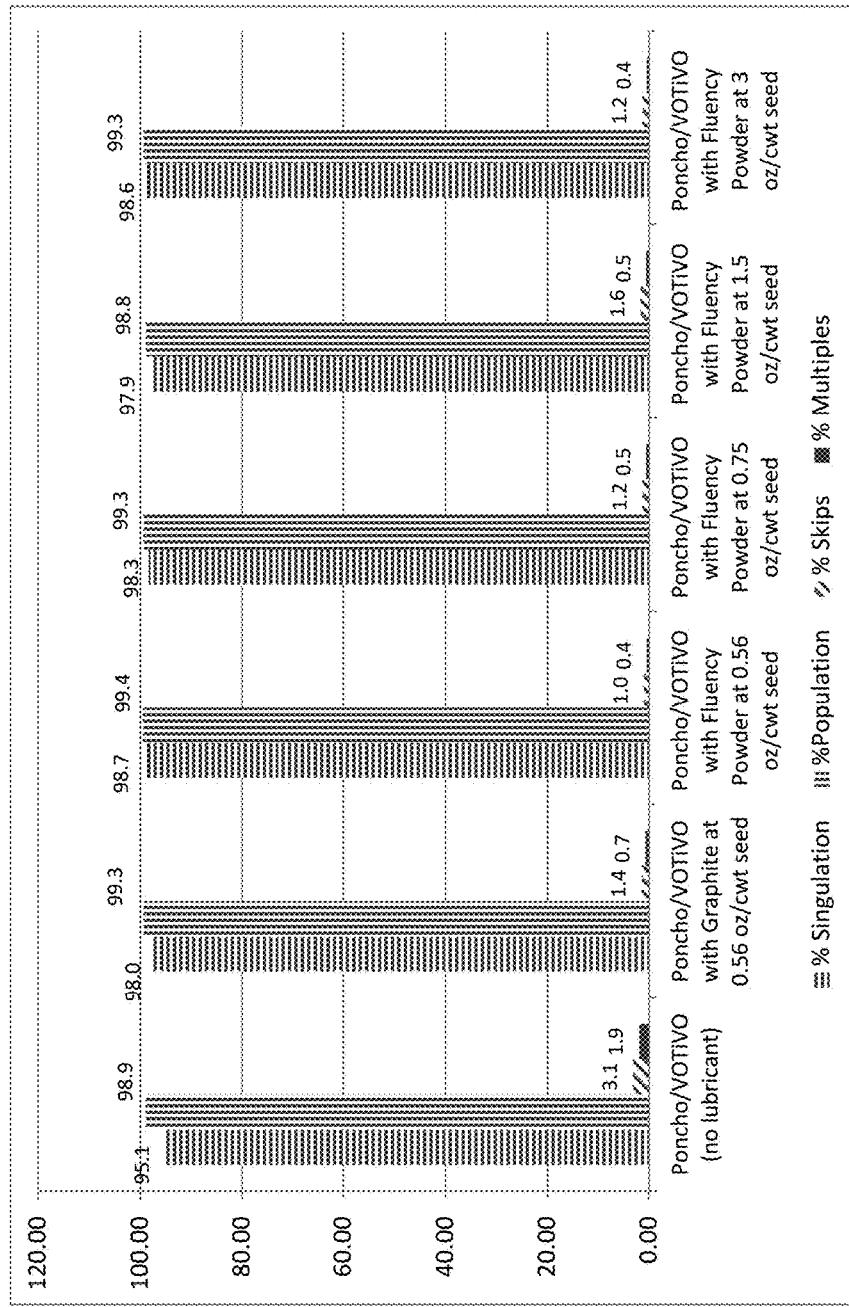
FIG. 2 sets forth corn dust levels for seeds treated with a Poncho/VOTiVO and talc treatment as compared to a treatment of Poncho/VOTiVO and oxidized polyethylene wax used as a lubricant at 0.56 oz/cwt seed, 0.75 oz/cwt seed, 1.5 oz/cwt seed, and 3 oz/cwt seed as measured by a John Deere Vacuum Meter.
Figure 3:
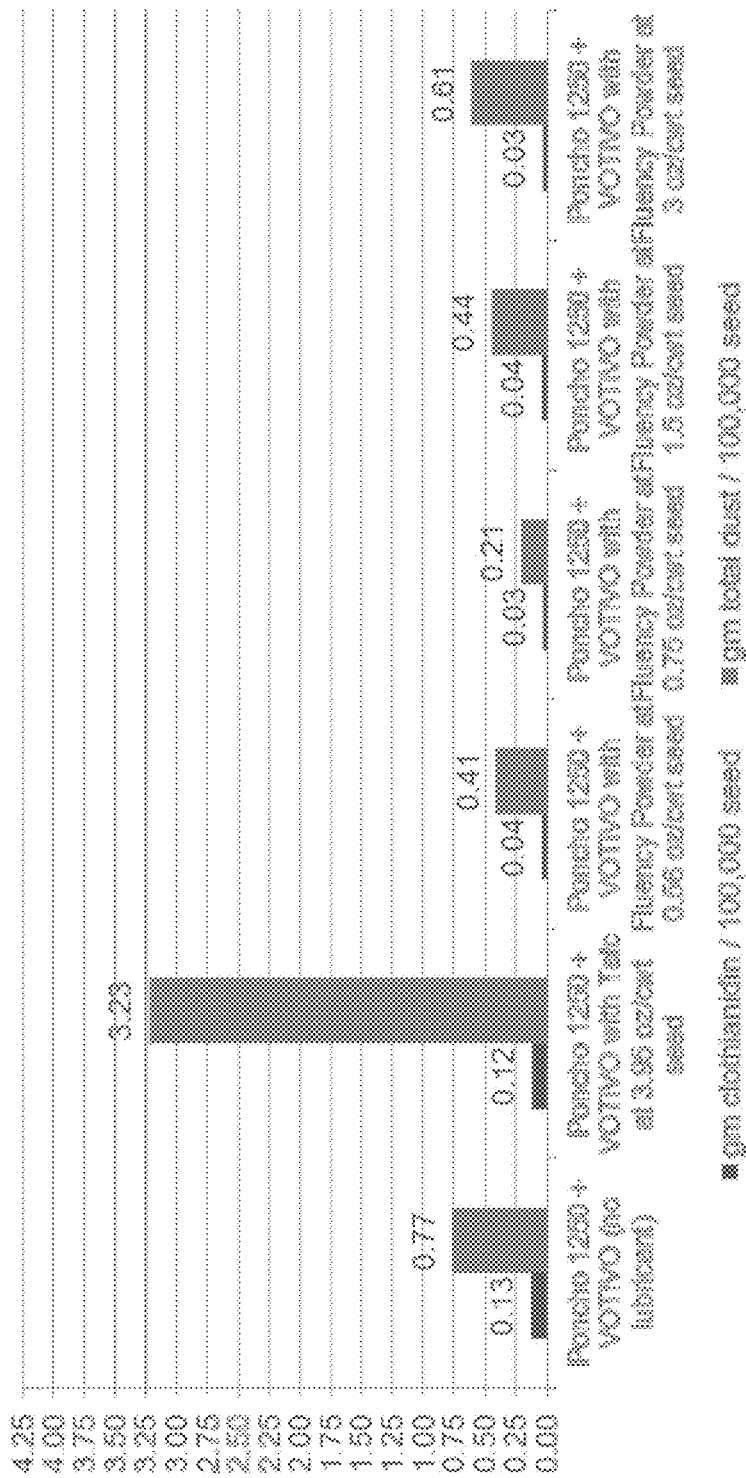
FIG. 3 sets forth the total grams of dust per 100,000 kernels and grams of clothianidin in total dust per 100,000 kernels for seeds treated with a Poncho 1250+VOTiVO and talc treatment as compared to a treatment of Poncho 1250+VOTiVO and oxidized polyethylene wax used as a lubricant at 0.56 oz/cwt seed, 0.75 oz/cwt seed, 1.5 oz/cwt seed, and 3 oz/cwt seed as measured by a John Deere Vacuum Meter.

In FIG. 2, the % Singulation, % Population, % Skips, and % Multiples were evaluated on a treatment combination of Poncho/VOTiVO and talc treatment as compared to a treatment combination of Poncho/VOTiVO and fluency powder (polyethylene wax) at 0.56 oz/cwt seed, 0.75 oz/cwt seed, 1.5 oz/cwt seed, and 3 oz/cwt seed. As set forth in FIG. 2, the % Singulation (the percentage of single distributed seeds spaced and planted in a manner that is consistent with the planter specification) and % Population (the number, in percent, of desired seeds that were planted in a manner that is consistent with the planter specification) of seeds coated with polyethylene wax as a lubricant were in line with those with as compared to talc. Additionally, as set forth in FIG. 2, the % Skips (the percentage of seeds that were not planted in a manner that is consistent with the planter specification) and the % Multiples (the percentage of multiple planted seeds) of seeds coated with an oxidized polyethylene wax as a lubricant were also in line with those with as compared to talc.

TABLE 1

| Treatment & Planter Lubricant | Total Grams dust per 100,000 kernels | Grams clothianidin in total dust per 100,000 kernels (HPLC analysis of filters) | % decrease of clothianidin in dust versus Talc |
| --- | --- | --- | --- |
| Poncho/VOTiVO (no lubricant) | 0.21 | 0.04 | −76% |
| Poncho/VOTiVO with Talc at 3.95 oz/cwt seed | 5.21 | 0.16 | Control |
| Poncho/VOTiVO with Fluency Powder at 0.56 oz/cwt seed | 0.20 | 0.03 | −84% |
| Poncho/VOTiVO with Fluency Powder at 0.75 oz/cwt seed | 0.10 | 0.02 | −88% |
| Poncho/VOTiVO with Fluency Powder at 1.5 oz/cwt seed | 0.17 | 0.02 | −89% |
| Poncho/VOTiVO with Fluency Powder at 3 oz/cwt seed | 0.41 | 0.02 | −86% |

In Table 2, the total grams of dust per 100,000 kernels and grams of clothianidin in total dust per 100,000 kernels for seeds treated with Poncho/VOTiVO and fluency powder (polyethylene wax) as a planter lubricant were evaluated. As set forth in Table 2, a treatment combination of Poncho/VOTiVO and talc treatment was compared to a treatment combination of Poncho/VOTiVO and fluency powder (oxidized polyethylene wax) at 0.56 oz/cwt seed, 0.75 oz/cwt seed, 1.5 oz/cwt seed, and 3 oz/cwt seed. The dust and clothianidin exposure were measured with a John Deere Vacuum Meter. The data in Table 2 represents an average of two seed sources. The data was measured by dust captured in the vacuum air stream coming out of the meter on the test stand.

TABLE 2

| Treatment & Planter Lubricant | Total Grams dust per 100,000 kernels | Grams clothianidin in total dust per 100,000 kernels (HPLC analysis of filters) | % decrease of clothianidin in dust versus Talc |
| --- | --- | --- | --- |
| Poncho/VOTiVO (no lubricant) | 0.89 | 0.09 | −19% |
| Poncho/VOTiVO with Talc at 3.95 oz/cwt seed | 4.21 | 0.11 | Control |
| Poncho/VOTiVO with Fluency Powder at 0.56 oz/cwt seed | 0.45 | 0.03 | −69% |
| Poncho/VOTiVO with Fluency Powder at 0.75 oz/cwt seed | 0.29 | 0.02 | −78% |
| Poncho/VOTiVO with Fluency Powder at 1.5 oz/cwt seed | 0.63 | 0.04 | −64% |
| Poncho/VOTiVO with Fluency Powder at 3 oz/cwt seed | 0.78 | 0.03 | −73% |

Example 2

Example 2 sets forth the Poncho 1250+VOTiVO Corn dust levels with polyethylene wax as a planter lubricant.

In Table 3, the total grams of dust per 100,000 kernels and grams of clothianidin in total dust per 100,000 kernels for seeds treated with Poncho 1250+VOTiVO and fluency powder (polyethylene wax) as a planter lubricant were evaluated. As set forth in Table 3, a treatment combination of Poncho 1250+VOTiVO and talc treatment was compared to a treatment combination of Poncho 1250+VOTiVO and fluency powder (polyethylene wax) at 0.56 oz/cwt seed, 0.75 oz/cwt seed, 1.5 oz/cwt seed, and 3 oz/cwt seed. The dust and clothianidin exposure were measured with a Heubach Dustmeter. The data in Table 3 represents an average of two seed sources.

Figure 4:
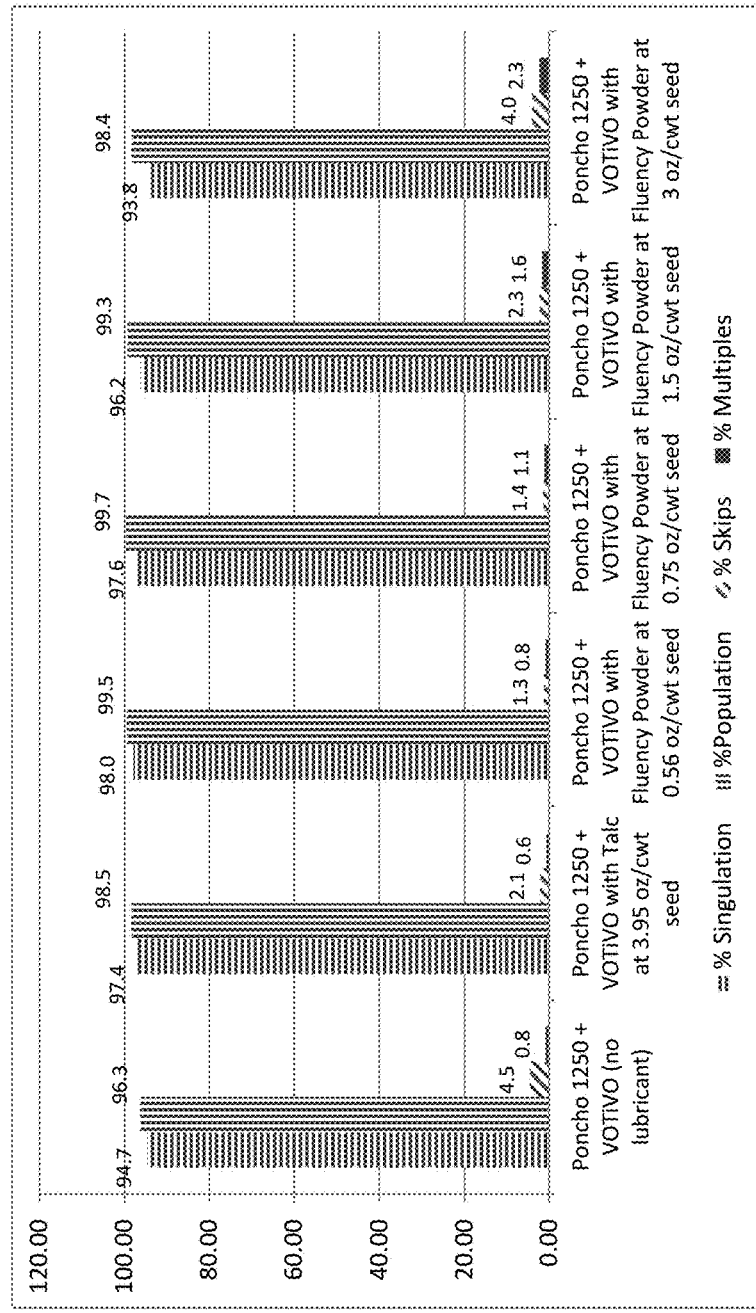
FIG. 4 sets forth measures corn dust levels for seeds treated with a Poncho 1250+VOTiVO and talc treatment as compared to a treatment of Poncho 1250+VOTiVO and polyethylene wax used as a lubricant at 0.56 oz/cwt seed, 0.75 oz/cwt seed, 1.5 oz/cwt seed, and 3 oz/cwt seed as measured by a John Deere Vacuum Meter.
Figure 5:
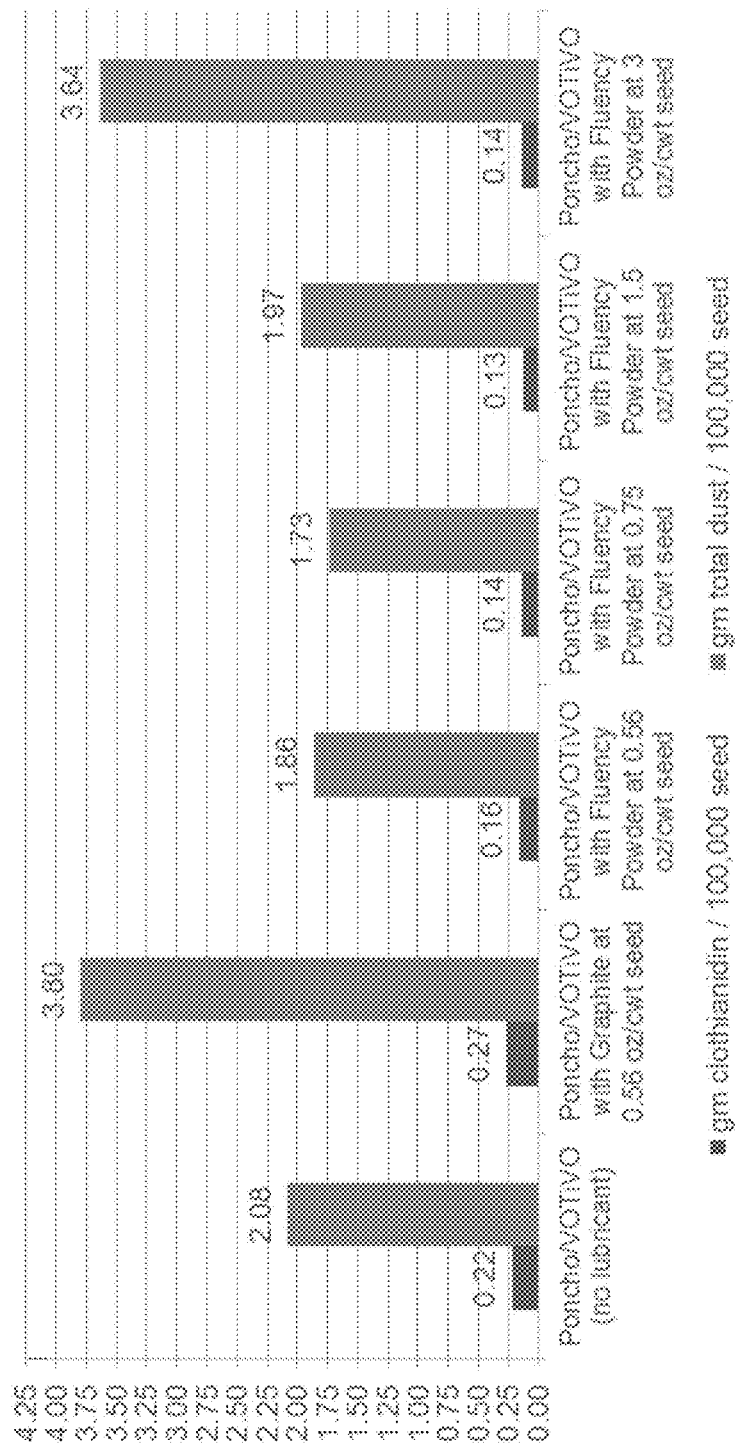
FIG. 5 sets forth the total grams of dust per 100,000 kernels and grams of clothianidin in total dust per 100,000 kernels for seeds treated with a Poncho/VOTiVO and graphite treatment as compared to a treatment of Poncho/VOTiVO and an oxidized polyethylene wax used as a lubricant at 0.56 oz/cwt seed, 0.75 oz/cwt seed, 1.5 oz/cwt seed, and 3 oz/cwt seed as measured by a Case IH Vacuum Meter.

In FIG. 4, the % Singulation, % Population, % Skips, and % Multiples were evaluated on a treatment combination of Poncho 1250+VOTiVO and talc treatment was compared to a treatment combination of Poncho 1250+VOTiVO and fluency powder (polyethylene wax) at 0.56 oz/cwt seed, 0.75 oz/cwt seed, 1.5 oz/cwt seed, and 3 oz/cwt seed. As set forth in FIG. 4, the % Singulation, % Population, % Skips, and % Multiples of seeds coated with polyethylene wax as a lubricant were in line with those with as compared to talc.

TABLE 3

| Treatment & Planter Lubricant | Total Grams dust per 100,000 kernels | Grams clothianidin in total dust per 100,000 kernels (HPLC analysis of filters) | % decrease of clothianidin in dust versus Talc |
|---|---|---|---|
| Poncho 1250 + VOTiVO (no lubricant) | 0.18 | 0.03 | −85% |
| Poncho 1250 + VOTiVO with Talc at 3.95 oz/cwt seed | 5.23 | 0.18 | Control |
| Poncho 1250 + VOTiVO with Fluency Powder at 0.56 oz/cwt seed | 0.06 | 0.01 | −95% |
| Poncho 1250 + VOTiVO with Fluency Powder at 0.75 oz/cwt seed | 0.07 | 0.01 | −96% |
| Poncho 1250 + VOTiVO with Fluency Powder at 1.5 oz/cwt seed | 0.10 | 0.01 | −94% |
| Poncho 1250 + VOTiVO with Fluency Powder at 3 oz/cwt seed | 0.09 | 0.01 | −93% |

In Table 4, the total grams of dust per 100,000 kernels and grams of clothianidin in total dust per 100,000 kernels for seeds treated with Poncho 1250+VOTiVO and fluency powder (oxidized polyethylene wax) as a planter lubricant were evaluated. As set forth in Table 4, a treatment combination of Poncho 1250+VOTiVO and talc treatment was compared to a treatment combination of Poncho 1250+VOTiVO and fluency powder (oxidized polyethylene wax) at 0.56 oz/cwt seed, 0.75 oz/cwt seed, 1.5 oz/cwt seed, and 3 oz/cwt seed. The dust and clothianidin exposure were measured with a John Deere Vacuum Meter. The data in Table 4 represents an average of two seed sources.

TABLE 4

| Treatment & Planter Lubricant | Total Grams dust per 100,000 kernels | Grams clothianidin in total dust per 100,000 kernels (HPLC analysis of filters) | % decrease or increase of clothianidin in dust versus Talc |
|---|---|---|---|
| Poncho 1250 + VOTiVO (no lubricant) | 0.77 | 0.13 | +7% |
| Poncho 1250 + VOTiVO with Talc at 3.95 oz/cwt seed | 3.23 | 0.12 | Control |
| Poncho 1250 + VOTiVO with Fluency Powder at 0.56 oz/cwt seed | 0.41 | 0.04 | −63% |
| Poncho 1250 + VOTiVO with Fluency Powder at 0.75 oz/cwt seed | 0.21 | 0.03 | −78% |
| Poncho 1250 + VOTiVO with Fluency Powder at 1.5 oz/cwt seed | 0.44 | 0.04 | −70% |
| Poncho 1250 + VOTiVO with Fluency Powder at 3 oz/cwt seed | 0.61 | 0.03 | −73% |

Example 3

Example 1 sets forth the Poncho/VOTiVO Corn dust levels with polyethylene wax as a planter lubricant.

In Table 5, the total grams of dust per 100,000 kernels and grams of clothianidin in total dust per 100,000 kernels for seeds treated with Poncho/VOTiVO and fluency powder (polyethylene wax) as a planter lubricant were evaluated. As set forth in Table 5, a treatment combination of Poncho/VOTiVO and graphite treatment was compared to a treatment combination of Poncho/VOTiVO and fluency powder (oxidized polyethylene wax) at 0.56 oz/cwt seed, 0.75 oz/cwt seed, 1.5 oz/cwt seed, and 3 oz/cwt seed. The dust and clothianidin exposure were measured with a Heubach Dustmeter. The data in Table 5 represents an average of two seed sources.

Figure 6:
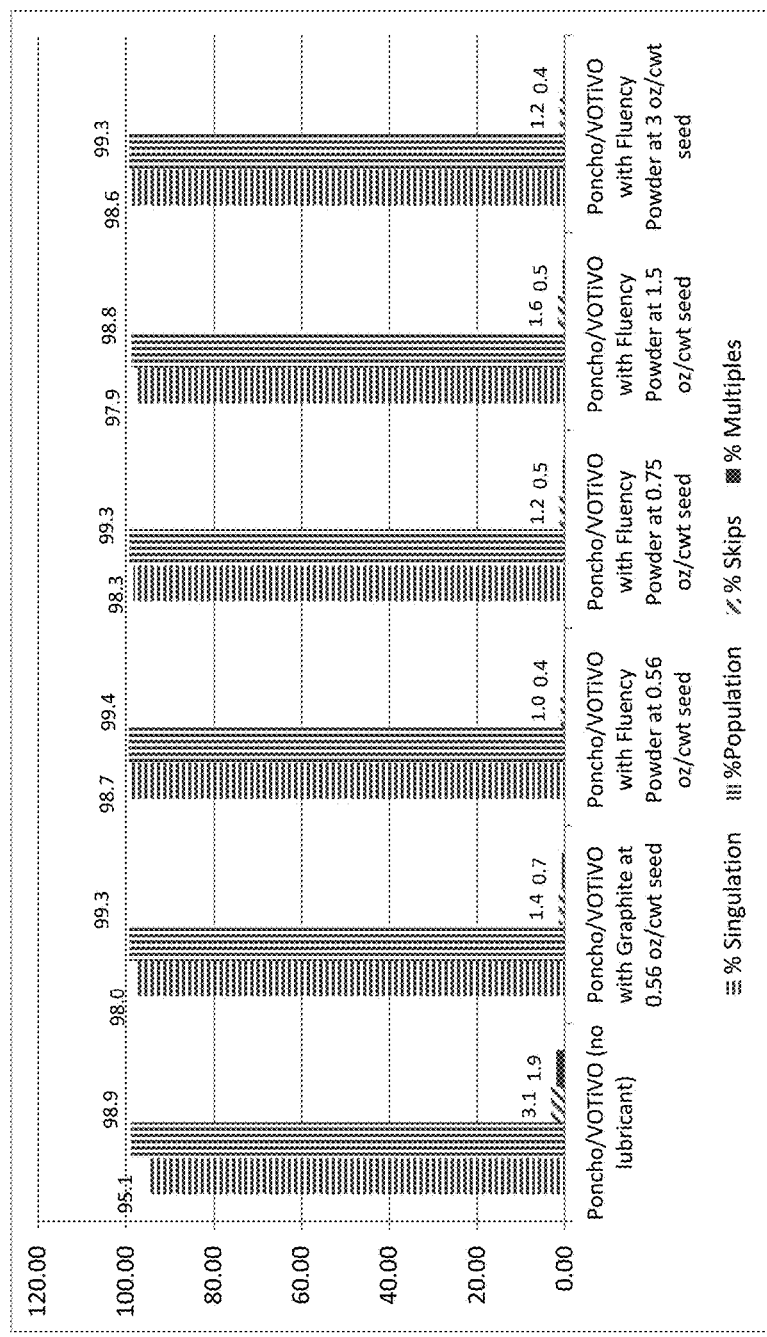
FIG. 6 sets forth measures corn dust levels for seeds treated with a Poncho/VOTiVO and graphite treatment as compared to a treatment of Poncho/VOTiVO and polyethylene wax used as a lubricant at 0.56 oz/cwt seed, 0.75 oz/cwt seed, 1.5 oz/cwt seed, and 3 oz/cwt seed as measured by a Case IH Vacuum Meter.
Figure 7:
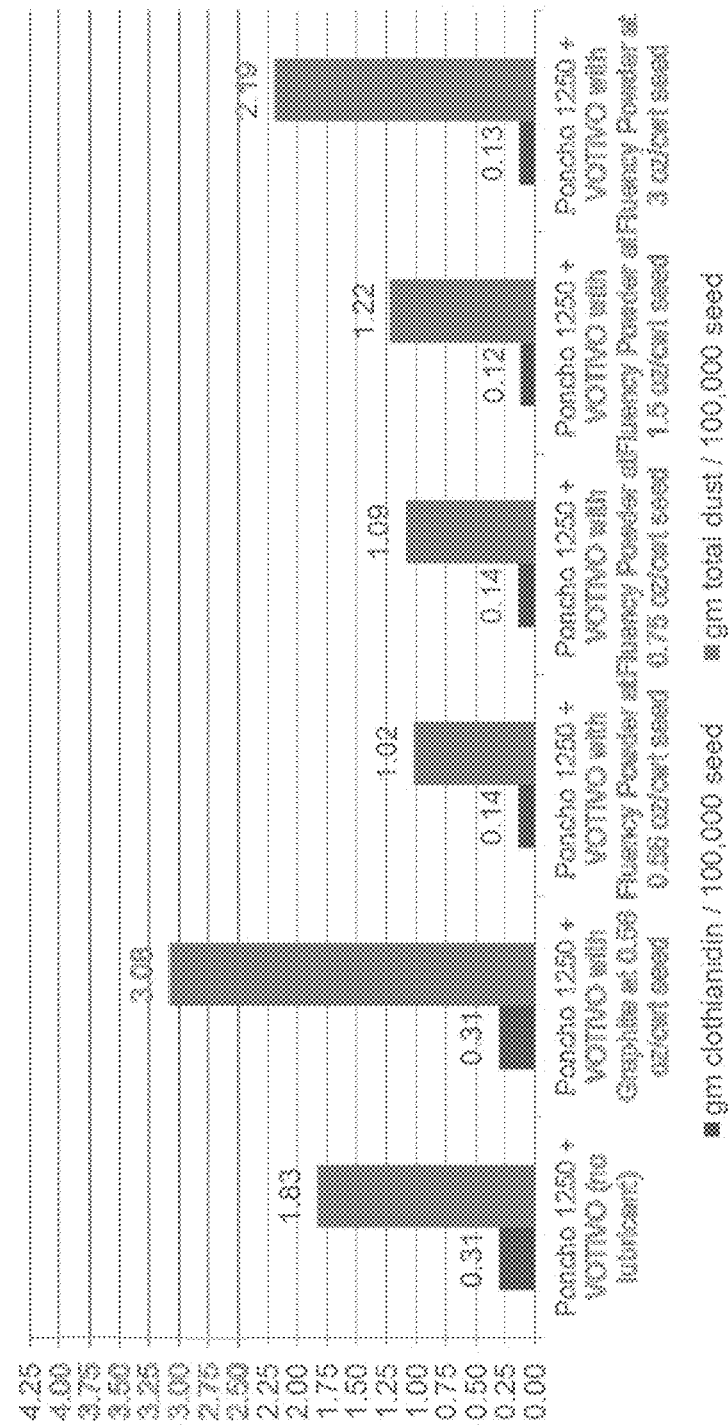
FIG. 7 sets forth the total grams of dust per 100,000 kernels and grams of clothianidin in total dust per 100,000 kernels for seeds treated with a Poncho 1250+VOTiVO and graphite treatment as compared to a treatment of Poncho 1250+VOTiVO and an oxidized polyethylene wax used as a lubricant at 0.56 oz/cwt seed, 0.75 oz/cwt seed, 1.5 oz/cwt seed, and 3 oz/cwt seed as measured by a Case IH Vacuum Meter.

In FIG. 6, the % Singulation, % Population, % Skips, and % Multiples were evaluated on a treatment combination of Poncho/VOTiVO and graphite treatment as compared to a treatment combination of Poncho/VOTiVO and fluency powder (oxidized polyethylene wax) at 0.56 oz/cwt seed, 0.75 oz/cwt seed, 1.5 oz/cwt seed, and 3 oz/cwt seed. As set forth in FIG. 6, the % Singulation, % Population, % Skips, and % Multiples of seeds coated with powdered oxidized polyethylene wax as a lubricant were in line with those with as compared to graphite.

TABLE 5

| Treatment & Planter Lubricant | Total Grams dust per 100,000 kernels | Grams clothianidin in total dust per 100,000 kernels (HPLC analysis of filters) | % decrease of clothianidin in dust versus Graphite |
|---|---|---|---|
| Poncho/VOTiVO (no lubricant) | 0.21 | 0.04 | −68% |
| Poncho/VOTiVO with Graphite at 0.56 oz/cwt seed | 0.92 | 0.12 | Control |
| Poncho/VOTiVO with Fluency Powder at 0.56 oz/cwt seed | 0.20 | 0.03 | −79% |
| Poncho/VOTiVO with Fluency Powder at 0.75 oz/cwt seed | 0.10 | 0.02 | −84% |
| Poncho/VOTiVO with Fluency Powder at 1.5 oz/cwt seed | 0.17 | 0.02 | −85% |
| Poncho/VOTiVO with Fluency Powder at 3 oz/cwt seed | 0.41 | 0.02 | −81% |

In Table 6, the total grams of dust per 100,000 kernels and grams of clothianidin in total dust per 100,000 kernels for seeds treated with Poncho/VOTiVO and fluency powder (polyethylene wax) as a planter lubricant were evaluated. As set forth in Table 6, a treatment combination of Poncho/VOTiVO and graphite treatment was compared to a treatment combination of Poncho/VOTiVO and fluency powder (oxidized polyethylene wax) at 0.56 oz/cwt seed, 0.75 oz/cwt seed, 1.5 oz/cwt seed, and 3 oz/cwt seed. The dust and clothianidin exposure were measured with a Case IH Vacuum Meter. The data in Table 6 represents an average of two seed sources.

TABLE 6

| Treatment & Planter Lubricant | Total Grams dust per 100,000 kernels | Grams clothianidin in total dust per 100,000 kernels (HPLC analysis of filters) | % decrease of clothianidin in dust versus Graphite |
|---|---|---|---|
| Poncho/VOTiVO (no lubricant) | 2.08 | 0.22 | −21% |
| Poncho/VOTiVO with Graphite at 0.56 oz/cwt seed | 3.80 | 0.27 | Control |
| Poncho/VOTiVO with Fluency Powder at 0.56 oz/cwt seed | 1.86 | 0.16 | −41% |
| Poncho/VOTiVO with Fluency Powder at 0.75 oz/cwt seed | 1.73 | 0.14 | −48% |
| Poncho/VOTiVO with Fluency Powder at 1.5 oz/cwt seed | 1.97 | 0.13 | −53% |
| Poncho/VOTiVO with Fluency Powder at 3 oz/cwt seed | 3.64 | 0.14 | −51% |

Example 4

Example 4 sets forth the Poncho 1250+VOTiVO Corn dust levels with polyethylene wax as a planter lubricant.

In Table 7, the total grams of dust per 100,000 kernels and grams of clothianidin in total dust per 100,000 kernels for seeds treated with Poncho 1250+VOTiVO and fluency powder (polyethylene wax) as a planter lubricant were evaluated. As set forth in Table 3, a treatment combination of Poncho 1250+VOTiVO and graphite treatment was compared to a treatment combination of Poncho 1250+VOTiVO and fluency powder (oxidized polyethylene wax) at 0.56 oz/cwt seed, 0.75 oz/cwt seed, 1.5 oz/cwt seed, and 3 oz/cwt seed. The dust and clothianidin exposure were measured with a Heubach Dustmeter. The data in Table 7 represents an average of two seed sources.

Figure 8:
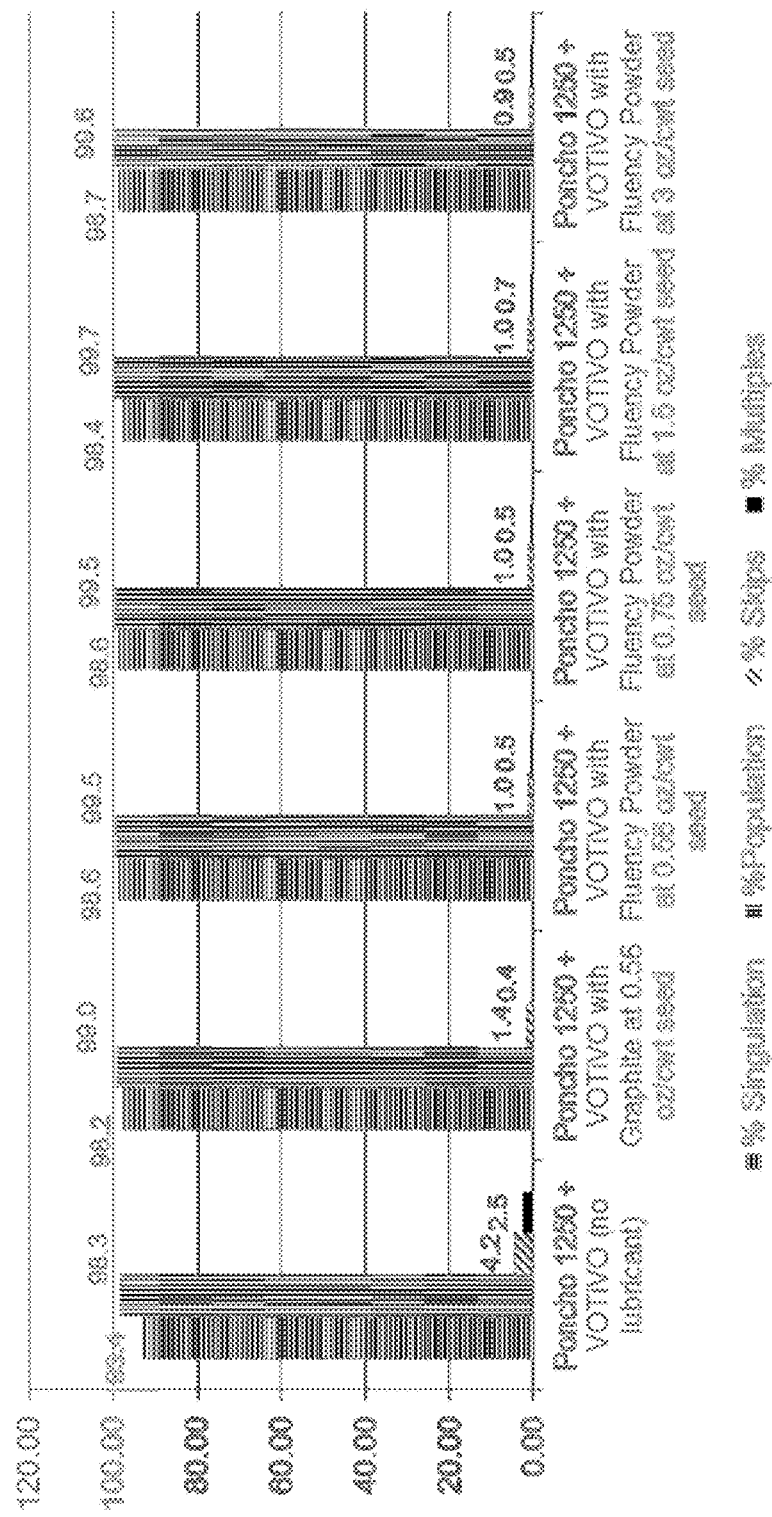
FIG. 8 sets forth measures corn dust levels for seeds treated with a Poncho 1250+VOTiVO and talc treatment as compared to a treatment of Poncho 1250+VOTiVO and an oxidized polyethylene wax used as a lubricant at 0.56 oz/cwt seed, 0.75 oz/cwt seed, 1.5 oz/cwt seed, and 3 oz/cwt seed as measured by a Case IH Vacuum Meter.

In FIG. 8, the % Singulation, % Population, % Skips, and % Multiples were evaluated on a treatment combination of Poncho 1250+VOTiVO and graphite treatment as compared to a treatment combination of Poncho 1250+VOTiVO and fluency powder (oxidized polyethylene wax) at 0.56 oz/cwt seed, 0.75 oz/cwt seed, 1.5 oz/cwt seed, and 3 oz/cwt seed. As set forth in FIG. 8, the % Singulation, % Population, % Skips, and % Multiples of seeds coated with powdered oxidized polyethylene wax as a lubricant were in line with those with as compared to graphite.

TABLE 7

| Treatment & Planter Lubricant | Total Grams dust per 100,000 kernels | Grams clothianidin in total dust per 100,000 kernels (HPLC analysis of filters) | % decrease of clothianidin in dust versus Graphite |
|---|---|---|---|
| Poncho 1250 + VOTiVO (no lubricant) | 0.18 | 0.03 | −69% |
| Poncho 1250 + VOTiVO with Graphite at 0.56 oz/cwt seed | 0.63 | 0.09 | Control |
| Poncho 1250 + VOTiVO with Fluency Powder at 0.56 oz/cwt seed | 0.06 | 0.01 | −89% |
| Poncho 1250 + VOTiVO with Fluency Powder at 0.75 oz/cwt seed | 0.17 | 0.01 | −91% |
| Poncho 1250 + VOTiVO with Fluency Powder at 1.5 oz/cwt seed | 0.10 | 0.01 | −88% |
| Poncho 1250 + VOTiVO with Fluency Powder at 3 oz/cwt seed | 0.09 | 0.01 | −86% |

In Table 8, the total grams of dust per 100,000 kernels and grams of clothianidin in total dust per 100,000 kernels for seeds treated with Poncho 1250+VOTiVO and fluency powder (polyethylene wax) as a planter lubricant were evaluated. As set forth in Table 8, a treatment combination of Poncho 1250+VOTiVO and graphite treatment was compared to a treatment combination of Poncho 1250+VOTiVO and fluency powder (oxidized polyethylene wax) at 0.56 oz/cwt seed, 0.75 oz/cwt seed, 1.5 oz/cwt seed, and 3 oz/cwt seed. The dust and clothianidin exposure were measured with a Case IH Vacuum Meter. The data in Table 8 represents an average of two seed sources.

TABLE 8

| Treatment & Planter Lubricant | Total Grams dust per 100,000 kernels | Grams clothianidin in total dust per 100,000 kernels (HPLC analysis of filters) | % decrease of clothianidin in dust versus Graphite |
|---|---|---|---|
| Poncho 1250 + VOTiVO (no lubricant) | 1.83 | 0.31 | −1% |
| Poncho 1250 + VOTiVO with Graphite at 0.56 oz/cwt seed | 3.08 | 0.31 | Control |
| Poncho 1250 + VOTiVO with Fluency Powder at 0.56 oz/cwt seed | 1.02 | 0.14 | −55% |
| Poncho 1250 + VOTiVO with Fluency Powder at 0.75 oz/cwt seed | 1.09 | 0.14 | −55% |
| Poncho 1250 + VOTiVO with Fluency Powder at 1.5 oz/cwt seed | 1.22 | 0.12 | −63% |
| Poncho 1250 + VOTiVO with Fluency Powder at 3 oz/cwt seed | 2.19 | 0.13 | −57% |

The invention claimed is:
1. A method of reducing seed dust comprising
   (a) first treating a corn, soybean or cotton seed with clothianidin or imidacloprid to produce pre-treated seed;
   (b) then applying an organic lubricant composition consisting essentially of powdered polyethylene wax to said pre-treated seed;

wherein seed dust from (1) said pre-treated seed with the applied organic lubricant composition is reduced relative to (2) seed of the same type pre-treated with clothianidin or imidacloprid with an applied coating of talc and/or graphite and without said organic lubricant composition, and wherein the organic lubricant composition is applied about 0.5-4.0 ounces per 100 pounds of seed, and wherein the seed dust is measured by a Heubach Dustmeter.

2. The method of claim 1, wherein said seed is corn seed.

3. The method of claim 2, comprising planting said seed with a mechanical planter, wherein said mechanical planter is an air or vacuum planter.

4. The method of claim 1, wherein seed to which the organic lubricant composition is applied reduces seed dust emissions by 50% or more.

5. The method of claim 1, wherein the seed is soybean seed.

6. The method of claim 1, wherein said organic lubricant is applied to said pre-treated seed in a planter mechanism or hopper of the planting mechanism.

* * * * *